United States Patent [19]

Tohzuka et al.

[11] 4,238,416

[45] Dec. 9, 1980

[54] METHOD FOR ISOMERIZATION OF FLUORINATED EPOXY COMPOUNDS

[75] Inventors: Takashi Tohzuka; Yohnosuke Ohsaka, both of Osaka, Japan

[73] Assignee: Daikin Kogyo Co., Ltd., Osaka, Japan

[21] Appl. No.: 7,239

[22] Filed: Jan. 29, 1979

Related U.S. Application Data

[63] Continuation-in-part of Ser. No. 826,247, Aug. 19, 1977, abandoned.

[30] Foreign Application Priority Data

Aug. 21, 1976 [JP] Japan .................................. 51-99849

[51] Int. Cl.$^3$ .............................................. C07C 45/58
[52] U.S. Cl. ................................. 568/384; 568/419
[58] Field of Search ........... 260/593 H, 580 R, 601 H

[56] References Cited

U.S. PATENT DOCUMENTS

| | | | |
|---|---|---|---|
| 3,321,515 | 5/1967 | Moore et al. | 260/593 H |
| 3,338,978 | 8/1967 | Moore | 260/593 H |
| 3,391,119 | 7/1968 | Anderson | 260/593 H |
| 3,959,367 | 5/1976 | Jeffrey | 260/348.32 |
| 4,057,584 | 11/1977 | Touzuka et al. | 260/593 H |

*Primary Examiner*—Natalie Trousof
*Assistant Examiner*—James H. Reamer
*Attorney, Agent, or Firm*—Stevens, Davis, Miller & Mosher

[57] ABSTRACT

A method for isomerization of fluorinated epoxy compounds by contacting with a catalyst to produce the corresponding fluorinated carbonyl compounds, which is characterized in that the catalyst is a fluorinated alumina or a fluorinated silica alumina.

4 Claims, No Drawings

METHOD FOR ISOMERIZATION OF FLUORINATED EPOXY COMPOUNDS

This is a continuation-in-part of application Ser. No. 826,247, filed Aug. 19, 1977 now abandoned.

The present invention relates to a method for isomerization of fluorinated epoxy compounds. More particularly, it relates to an improved method for catalytic isomerization of fluorinated epoxy compounds to the corresponding fluorinated carbonyl compounds.

Fluorinated carbonyl compounds have various uses. For instance, fluoroalkanones are useful as intermediates in the synthesis of a variety of fluorohydrocarbons due to the ready addition of hydroxyl group-containing compounds such as water or alcohols to the carbonyl group, and their hydrates are useful as solvents or plasticizers for polyamides, acetal resins and the like. Further, for instance, acid fluorides can be changed to fluorine-containing acids, esters amides and the like, most of which are useful as surfactants.

Fluorinated carbonyl compounds have usually been prepared by catalytic isomerization of the corresponding fluorinated epoxy compounds. As the catalyst for such isomerization, there are known $SbF_5$, $Al_2O_3$, $TiO_2$, $WO_2$, $AlCl_3$, $AlBr_3$, $SnCl_4$, $FeCl_3$, $ZrOCl_2$, $KF$, $KHF_2$, $PF_5$, etc. (cf. U.S. Pat. Nos. 3,213,134 and 3,321,515). However, these catalysts are not satisfactory in the conversion of the starting fluorinated epoxy compounds, and the yield of the produced fluorinated carbonyl compound is low.

As the result of the extensive study, it has now been found that a fluorinated alumina or a fluorinated silica alumina can izomerize fluorinated epoxy compounds into the corresponding fluorinated carbonyl compounds with a high conversion and an excellent yield. This invention is based on the said finding.

According to the present invention, there is provided a method for isomerization of a fluorinated epoxy compound to the corresponding fluorinated carbonyl compound by contacting the former with a catalyst, characterized in that the catalyst is a fluorinated alumina or a fluorinated silica alumina.

The starting fluorinated epoxy compounds are representable by the formula:

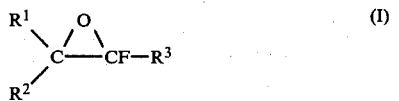

(I)

wherein $R^1$, $R^2$ and $R^3$ are each a fluorine atom, a $C_1$-$C_2$ perfluoroalkyl group or a $C_1$-$C_2$ ω-hydroperfluoroalkyl group, or two of them are linked together to form a $C_2$-$C_4$ perfluoroalkylene group. They are generally known and can be produced, for instance, by reacting the corresponding perfluoroalkenes with hydrogen peroxide in an inert solvent (e.g. methanol, ethanol) under an alkaline condition at a temperature of from about −35° to 50° C.

The catalyst to be used in the method of this invention is a fluorinated alumina or a fluorinated silica alumina.

As the fluorinated alumina, there may be used any material known as "fluorinated alumina." Some of the fluorinated alumina are known as catalysts in reforming of hydrocarbons, and some others are known as catalysts in rearrangement of chlorofluorohydrocarbons. The fluorinated alumina comprises aluminum, fluorine and oxygen as the essential components, and its fluorine content is desired to be from about 0.5 to 50% by weight, preferably from about 3 to 50% by weight.

The fluorinated alumina as the catalyst is ordinarily prepared by treatment of activated alumina with a fluorinating agent. As the activated alumina, there can be employed, without particular limitation, any conventional one such as natural alumina or synthetic alumina, e.g. highly porous alumina obtained by calcining α-alumina hydrate or β-alumina hydrate under appropriately controlled conditions. Some of commercially available activated alumina contain silica as the component for tablet-formation.

As the fluorinating agent, there may be used an inorganic fluorinating agent or an organic fluorinating agent. Examples of the inorganic fluorinating agent are hydrogen fluoride, silicon tetrafluoride, sulfur fluoride (e.g. sulfur tetrafluoride, sulfur hexafluoride), sulfuryl fluoride, thionyl fluoride, ammonium fluoride (e.g. acidic ammonium fluoride, neutral ammonium fluoride), etc. Examples of the organic fluorinating agent include fluorohydrocarbons, chlorofluorohydrocarbons, bromofluorohydrocarbons, etc. Fluorine-containing compounds of the formula: $C_nF_aH_bX$ wherein X is an oxygen atom or a nitrogen atom, n is an integer of 1 to 8 (preferably 1 to 4), a is an integer of 1 to $2n+m$, b is an integer of 0 to $2n+m-1$ and m is an integer of 2 when X is an oxygen atom or an integer of 3 when X is a nitrogen atom, as disclosed in Japanese Patent Publication (unexamined) No. 1578/1972, can be also used as the organic fluorinating agent. The fluorohydrocarbons may be saturated or unsaturated hydrocarbons having not more than 8, preferably not more than 4, carbon atoms in which at least one hydrogen atom is substituted with a fluorine atom. A higher degree of substitution with fluorine atoms is more preferable. Specific examples are $CF_4$, $CHF_3$, $CF_3CF_3$, $CHF_2CF_3$, $CHF_2CHF_2$, $CH_3CF_3$, $CH_2FCHF_2$, $CH_2=CF_2$, $CF_3CF=CF_2$, $CF_2=CF_2$, etc. The chlorofluorohydrocarbons and the bromofluorohydrocarbons may be saturated or unsaturated hydrocarbons having not more than 8, preferably not more than 4, carbon atoms in which hydrogen atoms are substituted with at least one fluorine atoms and at least one chlorine or bromine atom and include specifically $CCl_3F$, $CCl_2F_2$, $CHCl_2F$, $CHClF_2$, $CClF_2CCl_2F$, $CCl_3CF_3$, $CCl_2FCCl_2F$, $CCl_3CCl_2F$, $CClF_2CClF_2$, $CCl_2FCF_3$, $CF_3CCl=CClCF_3$, $CF_2BrCFClBr$, $CF_2BrCHClF$, $CF_2BrCF_2Br$, etc. Examples of the fluorine-containing compounds are hexafluoroacetone, hexafluoro-1,2-epoxyethane, decafluorodiethyl ether, tri(trifluoromethyl)amine, tetrafluoroethyl methyl ether, etc. Among them, perfluoroalkanes such as tetrafluoromethane and perfluoroalkenes such as hexafluoropropene are particularly preferred.

The preparation of the catalyst may be carried out by various procedures depending on the kind of the fluorinating agent as employed.

When, for instance, hydrogen fluoride or ammonium fluoride is employed as the fluorinating agent, the activated alumina is contacted with it at a temperature of about 20 to 450° C. so as to give the fluorinated alumina.

When sulfur fluoride, sulfuryl fluoride or thionyl fluoride is employed, the activated alumina may be contacted with the fluorinating agent at a temperature of about 300 to 500° C. to give the fluorinated alumina.

In some cases, sulfurous compounds may be formed and deposited on the catalyst, but they are not piosonous to the catalytic activity.

When the fluorinating agent is an organic fluorinating agent, the activated alumina may be contacted with it at a temperature of about 100 to 600° C., preferably of about 150° to 450° C. to give the desired fluorinated alumina.

In case of using an organic fluorinating agent, the treatment of the activated alumina with a chlorohydrocarbon or a bromohydrocarbon may be effected prior to the contact with the organic fluorinating agent. The coexistence of a chlorohydrocarbon or a bromohydrocarbon on the contact of the activated alumina with the organic fluorinating agent is sometimes recommendable, since the fluorination of the activated alumina can be accomplished more smoothly under a lower temperature.

As the chlorohydrocarbon or the bromohydrocarbon, there may be employed a saturated or unsaturated hydrocarbon having not more than 8, preferably not more than 4, carbon atoms in which at least one hydrogen atom is substituted with a chlorine or bromine atoms. A higher degree of substitution with chlorine or bromine atoms is more preferable. Substitution with chlorine or bromine atoms alone or with both of them is admissible. Specific examples are $CCl_4$, $CHCl_3$, $CCl_3CCl_3$, $CHCl_2CCl_3$, $CCl_2=CCl_2$, $CHCl=CCl_2$, $CHBr_3$, $CCl_2Br_2$, etc. Among them, perchlorohydrocarbons are particularly preferred.

Explaining the preparation of the fluorinated alumina by treatment of the activated alumina with the fluorohydrocarbon and the chlorohydrocarbon or the bromohydrocarbon, the activated alumina may be contacted first with the chlorohydrocarbon or the bromohydrocarbon at a temperature of about 100° to 400° C. (preferably 100 to 200° C.) and then with the fluorohydrocarbon at a temperature of about 100° to 400° C. (preferably 100° to 350° C.), whereby the fluorinated alumina can be obtained.

Alternatively, the activated alumina may be contacted with a mixture of the chlorohydrocarbon or the bromohydrocarbon and the fluorohydrocarbon at a temperature of about 100° to 400° C. (preferably 200° to 300° C.). The mixing proportion of the chlorohydrocarbon or the bromohydrocarbon to the fluorohydrocarbon is determined depending on their kinds. In the combination of tetrachloromethane and trichlorotrifluoroethane, for instance, the molar ratio of tetrachloromethane and trichlorotrifluoroethane is desired to be about 0.1–5:1.

In addition to the procedures as above, the fluorinated alumina may be produced by any conventional procedure, for instance, as described in Japanese Patent Publications Nos. 11605/1964 and 27748/1968.

The fluorinated silica alumina comprises aluminum, silicon, fluorine and oxygen as the essential components, and the desirable fluorine content is from about 0.5 to 50% by weight, particularly from about 3 to 50% by weight.

The fluorinated silica alumina may be prepared by treatment of silica alumina with a fluorinating agent in the substantially same manner as adopted in the preparation of the fluorinated alumina. The starting silica alumina is per se well known and may have an alumina content usually of not less than about 10% by weight, preferably of not less than about 25% by weight. As the fluorinating agent, there may be employed the one as mentioned above in connection with the preparation of the fluorinated alumina.

When the catalyst is used for a long period of time, carbonaceous materials are deposited on its surface to lower the catalytic activity. In such case, the catalytic activity can be recovered by heating the catalyst in the presence of oxygen or an oxygen-containing material such as air at a temperature of about 350° to 500° C.

The process of the invention can be effected by contacting the fluorinated epoxy compound with the fluorinated alumina or the fluorinated silica-alumina as the catalyst in a per se conventional manner. Thus, the fluorinated epoxy compound may be contacted with a fixed bed, moving bed or fluidized bed of the catalyst in an appropriate reaction vessel or tube in a continuous system or a closed system.

On the contact, the fluorinated epoxy compound may be previously diluted with any gaseous material. Examples of the gaseous material for dilution are inert gases (e.g. nitrogen, carbon dioxide), oxygen, air, etc. Among them, the use of oxygen or an oxygen-containing gas such as a mixture of oxygen with an inert gas is preferred in preventing the catalyst from the inactivation. The molar ratio of the fluorinated epoxy compound and oxygen may be usually 1:0.1–2.0.

The reaction temperature at the contact is varied with the kind of the fluorinated epoxy compound and may be usually from about 100° to 200° C.

As to the reaction pressure, there is present no particular limitation, and it may be usually from about 0.5 to 5 atmospheric pressure.

As the result of the contact, there are produced various fluorinated carbonyl compounds depending on the starting fluorinated epoxy compounds, and the relationships between the starting fluorinated epoxy compounds and the produced fluorinated carbonyl compounds may be classified as follows:

(1) When the starting fluorinated epoxy compound is the one of the formula (I) wherein $R^1$, $R^2$ and $R^3$ are each a fluorine atom:

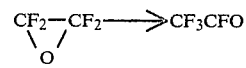

(2) When the starting fluorinated epoxy compound is the one of the formula (I) wherein $R^1$ is a perfluoroalkyl group or an $\omega$-hydroperfluoroalkyl group and $R^2$ and $R^3$ are each a fluorine atom:

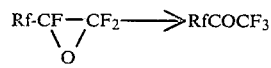

(3) When the starting fluorinated epoxy compound is the one of the formula (I) wherein $R^1$ and $R^3$ are each a perfluoroalkyl group or an $\omega$-hydroperfluoroalkyl group and $R^2$ is a fluorine atom:

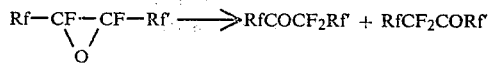

(4) When the starting fluorinated epoxy compound is the one of the formula (I) wherein $R^1$ and $R^2$ are each a perfluoroalkyl group or an $\omega$-hydroperfluoroalkyl group and $R^3$ is a fluorine atom:

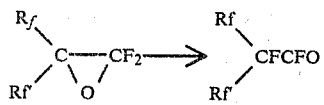

(5) When the starting fluorinated epoxy compound is the one of the formula (I) wherein $R^1$, $R^2$ and $R^3$ are each a perfluoroalkyl group or an ω-hydroperfluoroalkyl group:

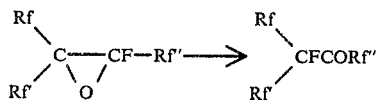

(wherein Rf, Rf' and Rf'' are each a perfluoroalkyl group or an ω-hydroperfluoroalkyl group).

Still, the substantially same relationships as above are applicable to the compounds wherein two of $R^1$, $R^2$ and $R^3$ are linked together to form a perfluoroalkylene group.

Practical and presently preferred embodiments of this invention are illustratively shown in the following Examples.

EXAMPLE 1

Fluorinated alumina (fluorine content, 10% by weight; particle size, 2 to 4 mm) (35 g) was charged into a reaction tube made of Pyrex glass and being 22 mm in inner diameter and 1,000 mm in length. The reaction tube was heated to 170° C., and hexafluoro-1,2-epoxypropane

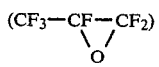

and nitrogen were respectively introduced into the reaction tube at a rate of 60 ml/min (0° C., 1 atm.) with a total pressure of 1 atm. After 1 hour, the produced gas discharged from the reaction tube was subjected to gas chromatographic analysis, and it was confirmed that the conversion of hexafluoro-1,2-epoxypropane into hexafluoro-2-propanone was nearly 100%. The contact was continued for additional 2 hours so that the catalytic activity of the fluorinated alumina was almost lost.

EXAMPLE 2

The reaction tube charged with the fluorinated alumina almost lost the catalytic activity as obtained in Example 1 was heated at 450° C., and oxygen was passed through at a rate of 100 ml/min for 2 hours. Then, the reaction tube was kept at 170° C., and hexafluoro-1,2-epoxypropane, nitrogen and oxygen were introduced therein respectively at rates of 40 ml/min, 200 ml/min and 20 ml/min with a total pressure of 1 atm. After 1 hour, the produced gas discharged from the reaction tube was subjected to gas chromatographic analysis, whereby it was confirmed that the conversion of hexafluoro-1,2-epoxypropane into hexafluoro-2-propanone was nearly 100%. The contact was continued for additional 2 hours, but no material depression in the catalytic activity was produced.

EXAMPLE 3

Fluorinated alumina (fluorine content, 10% by weight; particle size, 2 to 4 mm) (35 g) was charged into a reaction tube made of Pyrex glass and being 22 mm in inner diameter and 1,000 mm in length. The reaction tube was heated to 170° C., and hexafluoro-1,2-epoxypropane, nitrogen and oxygen were respectively introduced therein at rates of 15 ml/min, 180 ml/min and 20 ml/min with a total pressure of 1 atm. After 3 hours, the produced gas discharged from the reaction tube was subjected to gas chromatographic analysis, and it was confirmed that the conversion of hexafluoro-1,2-epoxypropane into hexafluoro-2-propanone was nearly 100%.

The same procedure as above but using γ-alumina (particle size, 2 to 4 mm) (35 g) in place of the fluorinated alumina was carried out. After 3 hours, the produced gas discharged from the reaction tube was subjected to gas chromatographic analysis, and it was confirmed that the gas comprised 40 mol % of hexafluoro-1,2-epoxypropane and 60 mol % of hexafluoro-2-propanone.

EXAMPLE 4

The reaction tube charged with the fluorinated alumina as obtained in Example 3 was kept at 130° C., and hexafluoro-1,2-epoxypropane and oxygen were introduced therein respectively at a rate of 60 ml/min with a total pressure of 1 atm. After 3 hours, the produced gas discharged from the reaction tube was subjected to gas chromatographic analysis, and it was confirmed that the conversion of hexafluoro-1,2-epoxypropane into hexafluoro-2-propanone was nearly 100%.

EXAMPLE 5

Fluorinated alumina (fluorine content, 10% by weight; particle size, 2 to 4 mm) (35 g) was charged into a reaction tube made of Pyrex glass and being 22 mm in inner diameter and 1,000 mm in length. The reaction tube was heated to 110° C., and hexafluoro-1,2-epoxypropane, nitrogen and oxygen were respectively introduced therein at rates of 15 ml/min, 180 ml/min and 20 ml/min with a total pressure of 1 atm. After 3 hours, the produced gas discharged from the reaction tube was subjected to gas chromatographic analysis, and it was confirmed that the gas comprised 28 mol % of hexafluoro-1,2-epoxypropane and 72 mol % of hexafluoro-2-propanone.

EXAMPLE 6

Silica alumina ($SiO_2 : Al_2O_3 = 60 : 40$ by weight; particle size, 2 to 4 mm) (35 g) was charged into a reaction tube made of Pyrex glass and being 22 mm in inner diameter and 1,000 mm in length. The reaction tube was heated to 400° C. in nitrogen stream, and this temperature was maintained for 2 hours, during which dehydration was carried out. The temperature was then lowered to ;b 200° C., and $CCl_2F_2$ was introduced therein at a rate of 50 ml/min for 4 hours. Oxygen was introduced into the reaction tube at 300° C. for 1 hour, whereby fluorinated silica alumina was obtained. After cooling, a portion of the reaction product was subjected to analysis, whereby the fluorine content was confirmed to be 3.2% by weight. The reaction tube charged with the above obtained fluorinated silica alumina was heated to 170° C., and hexafluoro-1,2-epoxypropane, nitrogen and oxygen were respectively introduced therein at rates of 15 ml/min, 180 ml/min and 20 ml/min with a total pressure of 1 atm. After 3 hours, the produced gas discharged from the reaction tube was subjected to gas chromatographic analysis, and it was confirmed that the conversion of hexafluoro-1,2-epoxypropane into hexafluoro-2-propanone was nearly 100%.

What is claimed is:

1. In a method for the catalytic isomerization of a fluorinated epoxy compound to form the corresponding fluorinated carbonyl compound, the improvement which comprises conducting the isomerization in the presence of a catalyst selected from the group consisting of fluorinated alumina and fluorinated silica alumina and a gas containing oxygen.

2. The method according to claim 1, wherein the molar ratio of the fluorinated epoxy compound and oxygen is 1 : 0.1–2.0.

3. The method according to claim 1, wherein the contact is carried out at a temperature from about 100° to 200° C.

4. The method according to claim 1, wherein the fluorine content of the fluorinated alumina or the fluorinated silica alumina is from about 3 to 50% by weight.

* * * * *